Dec. 26, 1972
G. H. MACK ET AL
Plant Pat. 3,278
CHRYSANTHEMUM PLANT
Filed March 30, 1971
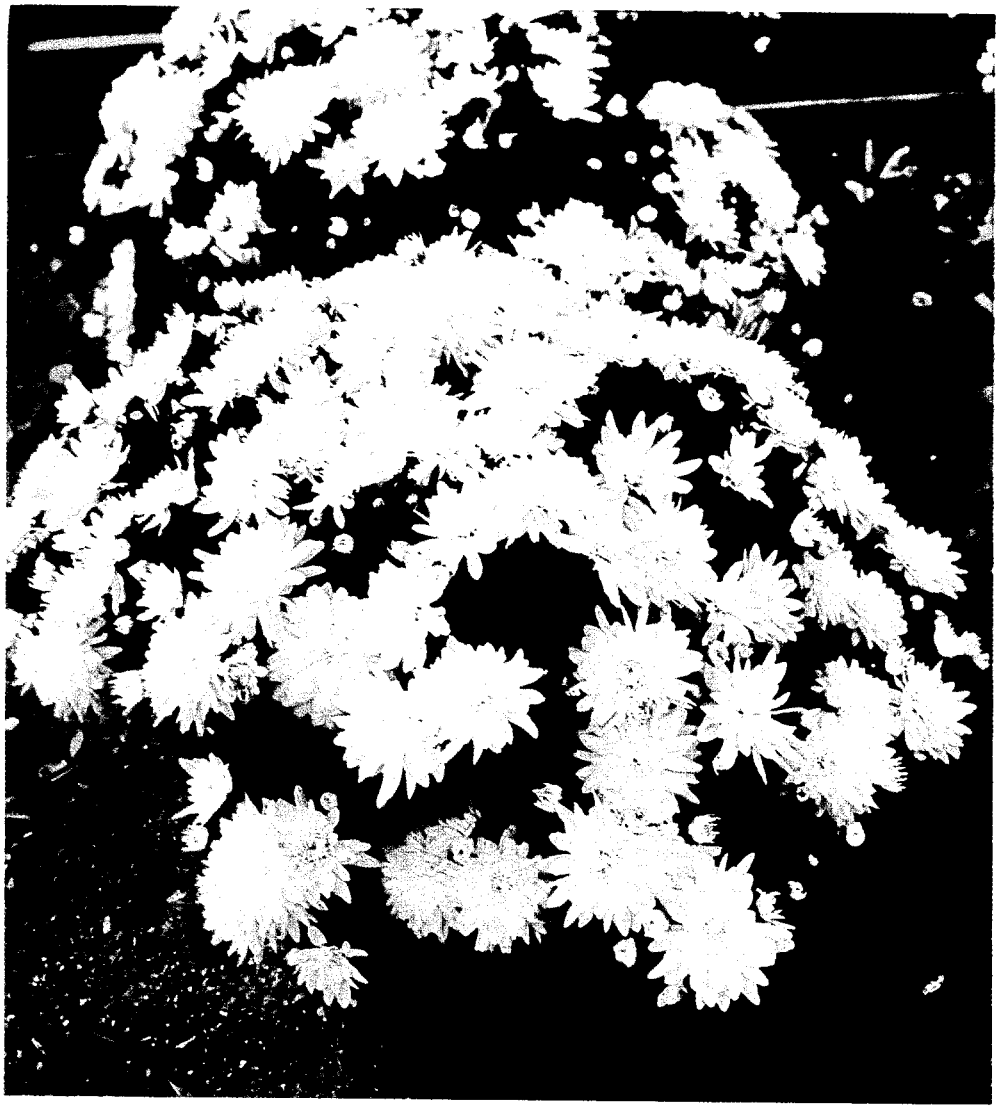
INVENTORS
GRACE H. MACK,
WALTER H. JESSEL, JR.,
WILLIAM E. DUFFETT
BY
Oberlin, Maky, Donnelly & Renner
ATTORNEYS

United States Patent Office

Plant Pat. 3,278

Patented Dec. 26, 1972

3,278
CHRYSANTHEMUM PLANT

Grace H. Mack, New Canaan, Conn., and Walter H. Jessel, Jr., Doylestown, and William E. Duffett, Akron, Ohio, assignors to Grace H. Mack, New Canaan, Conn.

Filed Mar. 30, 1971, Ser. No. 129,647

Int. Cl. A01h *5/00*

U.S. Cl. Plt.—75 1 Claim

The present invention comprises a new and distinct cultivar of garden variety chrysanthemum plant which is a seedling of Snowbound × #723–69. Both parents are unpatented and the numbered parent is identified by such number for breeding purposes to distinguish such parent from others in the same breeding program.

The new cultivar is similar in certain respects to White Grandchild, having the same spreading habit and flowering period.

The new cultivar is distinguished from White Grandchild by the following characteristics:

(1) Flowers are ¼″ larger, more ivory in color and do not tinge pink with age.

(2) 3″ shorter habit.

(3) Lighter colored foliage.

(4) More deeply indented leaf with a coarser serration to the leaf margin.

(5) More prominent stipules.

(6) 6 days longer keeping quality under outdoor conditions.

(7) Flowers approximately 5 to 6 days later than White Grandchild in outdoor natural season flowerings.

(8) Flowers approximately 2 to 3 days later in no light/no shade spring pot programs for May flowerings.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 7 weeks, and a natural flowering date of October 1. The following detailed description is based on observations made of the new cultivar in both a greenhouse and outdoors in Barberton, Ohio. The response time, blooming period, color, and total vigor may vary significantly with varying environmental conditions such as temperature, day length, and light intensity. Suggested flowering in the northern and western United States and coastal California is from mid-April through May and mid-September through mid-October.

The accompanying drawing shows the unique characteristics of the new cultivar, the color being as nearly true as possible with color illustrations of this type.

In the following description, color references are made to the Munsell Color Book, 1963 edition, and where only one value or description is listed, such value or description applies also to the comparison cultivar. Comparisons are made with the cultivar White Grandchild.

Botanical Classification: *Chrysanthemum morifolium*

| | Penguin | White Grandchild |
|---|---|---|
| Bloom: | | |
| Size | 1¾″ | 1½″. |
| Fully expanded | 2¼″ | 2″. |
| Borne | Clusters on elongated pedicels | Clusters on elongated pedicels. |
| Stems | Strong | Strong. |
| Form | Decorative | Decorative. |
| Permanence | 16 days | 10 days. |
| Color: | | |
| Center of flower | Ivory white, 10Y9/4 | White, N9.5/. |
| Base of petals | White, 10Y9/1 | Do. |
| Inside of petals | do | Do. |
| Reverse of petals | do | Do. |
| Tonality from a distance | White | White. |
| Discoloration | do | Light lavender pink, 7.5RP9/2 over white, N9.5/. |
| Petals: | | |
| Texture | Smooth | |
| Appearance and form | Open at base, broad, shallow ridged keel, tapering to a blunt point. | Open at base, broad shallow keel tapering to a blunt point. |
| Arrangement | Composite, whorled on a single receptacle | |
| Persistence | Resists shatter | |
| Fragrance | Typical chrysanthemum | |
| Reproductive organs: | | |
| Stamen, anthers | None | |
| Pollen | do | 0–20. |
| Arrangement | | None—Scant. |
| Styles | Clustered in center of flower, if present | |
| Length | Present both ray and disc florets | |
| Ovaries | Short | |
| Plant: | At the base of petal attached to receptacle | |
| Form | Herbaceous | |
| Growth | Compact—spreading | |
| Height | Approximately 12″ when flowered naturally as field grown plants from a planting made in mid-June and given a single pinch in late June. | Approximately 15″ when flowered naturally as field grown plants from a planting made in mid-June and given a single pinch in late June. |
| Spread | Approximately 22″ when flowered naturally as field grown plants from a planting made in mid-June and given a single pinch in late June. | Approximately 20″ when flowered naturally as field grown plants from a planting made in mid-June and given a single pinch in late June. |
| Foliage: | | |
| Top side | Dark green 7.5GY3/4 | Dark green, 10GY2/4. |
| Size | 3½″ long, 2½″ wide | 3″ long, 2″ wide. |
| Quantity | Numerous | Numerous. |
| Shape | Spatulate lobed | |
| Texture | Smooth | |
| Ribs and veins | Prominent | |
| Edge | Deeply indented | Moderately indented. |
| Serration | Coarse | Very slight. |
| Underside | Light green, 7.5GY5/4 | |
| Stipules | Prominent | Rudimentary. |

We claim:

1. A new and distinct cultivar of chrysanthemum characterized particularly as to its uniqueness when compared to the cultivar White Grandchild by its ¼″ larger flowers which have a more ivory color which does not tinge pink with age, 3″ shorter habit, lighter foliage, a more deeply indented leaf with a coarser serration to the leaf margin, more prominent stipules, and 6 days longer keeping quality under outdoor conditions.

No references cited.

ROBERT E. BAGWILL, Primary Examiner